United States Patent [19]

Zeigler, Jr.

[11] 4,352,699

[45] Oct. 5, 1982

[54] CO-NITRATING TRIMETHOLETHANE AND DIETHYLENE GLYCOL

[75] Inventor: Edward H. Zeigler, Jr., Budd Lake, N.J.

[73] Assignee: Hercules Incorporated, Wilmington, Del.

[21] Appl. No.: 269,154

[22] Filed: Jun. 1, 1981

[51] Int. Cl.$^3$ .................. D03D 23/00; D03D 43/00
[52] U.S. Cl. ......................... 149/109.6; 149/88; 260/467
[58] Field of Search ................ 149/88, 104, 109.6; 260/467

[56] References Cited

U.S. PATENT DOCUMENTS

| | | | |
|---|---|---|---|
| 3,238,074 | 3/1966 | Griffith et al. | 149/2 |
| 3,306,790 | 2/1967 | Crescenzo et al. | 149/93 |
| 3,423,256 | 1/1969 | Griffith | 149/2 |
| 3,639,183 | 2/1972 | Crescenzo et al. | 149/18 |
| 3,844,856 | 10/1974 | Flynn et al. | 149/19.8 |
| 3,951,706 | 4/1976 | Eldridge | 149/19.8 |

FOREIGN PATENT DOCUMENTS 382123  10/1932  United Kingdom ............... 149/104

*Primary Examiner*—Leland A. Sebastian
*Attorney, Agent, or Firm*—Marion C. Staves

[57] ABSTRACT

It has been discovered that when co-nitrating a mixture of trimethylolethane and diethylene glycol, a storage stable spent acid can be obtained if during the co-nitration an excess of from about 60 to about 100% by weight of nitric acid over that stoichiometrically required is employed.

3 Claims, No Drawings

CO-NITRATING TRIMETHOLETHANE AND DIETHYLENE GLYCOL

BACKGROUND OF THE INVENTION

1. Field of the Invention

This invention relates to a process of co-nitrating a mixture of trimethylolethane and diethylene glycol. More particularly this invention relates to a process of co-nitrating a mixture of trimethylolethane and diethylene glycol with an excess of from about 60 to about 100% by weight of nitric acid above the stoichiometric requirement.

2. Description of the Prior Art

Commercial explosives and gun propellants, based on nitroglycerine have been known and widely used for years. The nitroglycerine, alone or mixed with sensitizers such as nitroglycol, imparts desirable properties to explosive and propellant compositions. However, due to the very high sensitivity of nitroglycerine there are certain disadvantages in its use. Also nitroglycerine is a powerful vasodilator causing headaches among workers exposed to its vapor.

More recently explosive sensitizer compositions have been used which have lower impact sensitivity and often low vapor pressure. For example, U.S. Pat. No. 3,238,074 discloses explosive compositions containing up to 40% of a "known sensitizing explosive" used alone or in admixture. Among the sensitizing explosives recited in the patent are diethylene glycol dinitrate and trimethylolethane trinitrate. The mixture of diethylene glycol dinitrate and trimethylolethane trinitrate is also mentioned in a number of patents as energetic plasticizers in propellants. See, for example, U.S. Pat. Nos. 3,306,790; 3,639,183; 3,844,856; and 3,951,706.

The nitrate sensitizers are generally prepared by nitrating the polyols with nitric acid. For example, U.S. Pat. No. 3,423,256 discloses co-nitrating a mixture of a polyol, such as ethylene glycol, and trimethylolethane with a mixture of sulfuric and nitric acids. The patentee states that the amount of nitric acid employed is normally that stoichiometrically required to nitrate the free hydroxyl groups of the polyol. The patentee goes on to indicate that a small excess, ranging from about 5 to 25% can be used to ensure completion of the nitration.

Diethylene glycol and trimethylolethane can be co-nitrated in the usual way, as reported in the prior art, using the amount of nitric acid stoichiometrically required to nitrate the free hydroxyl groups or a small excess. However, if the normal nitration process if followed, one obtains a spent acid which is unstable and will decompose exothermically in a few hours.

SUMMARY OF THE INVENTION

It has now surprisingly been found that diethylene glycol and trimethylolethane can be co-nitrated and a storage stable spent acid obtained if one employes during the nitration an excess of from about 60 to about 100% by weight of nitric acid over that stoichiometrically required for the nitration. Accordingly, this invention relates to a process of co-nitrating a mixture of trimethylolethane and diethylene glycol with an excess of from about 60 to about 100% by weight of nitric acid above the stoichiometric required to nitrate the free hydroxyl groups.

DETAILED DESCRIPTION OF THE INVENTION

In general, useful concentration ranges of trimethylolethane and diethylene glycol for co-nitration will be from about 40 to about 60%, by weight of trimethylolethane and about 70 to about 30% by weight of diethylene glycol. The exact range used in any specific co-nitration will depend upon the specific properties of sensitivity, energy, density, freezing point, and solvent power desired in the nitrated product.

The process of this invention is conducted in conventional equipment adapted to handle acidic liquids in the usual liquid nitration procedure. The usual nitrating agent is concentrated nitric acid.

In the preferred process, a sufficient amount of sulfuric acid is blended with the concentrated nitric acid to form a reaction mixture in which the co-nitrate product is insoluble. Satisfactory proportions of nitric acid in a mixture of nitric and sulfuric acids are within the range of from about 90 to about 30% by weight, and of sulfuric acid, within the range of from about 10 to about 70% by weight. The reaction mixture can also contain up to about 10% by weight of water. Most preferably the proportion of concentrated nitric acid will be in the range of from about 55 to about 48% by weight and of sulfuric acid from about 45 to about 52% by weight. The amount of nitric acid used will be in excess of the stoichiometric amount required for co-nitration by from about 60 to about 100% by weight.

The co-nitration will be carried out at atmospheric pressure and at a temperature at which the nitration proceeds but below the temperature of decomposition of the co-nitrate reaction product. Since the reaction will proceed at a satisfactory speed at room temperature, the maximum temperature will generally be about 25° C. Preferably the reaction will be conducted at a temperature of from about 0° C. to about 20° C.

The reaction products of the process of this invention are useful as sensitizing explosives in any type of explosive formulation. They may be used in dynamites at levels of from about 5% by weight to about 95% by weight as a sensitizer, waterproofing agent, and nitrocellulose gellation agent in accordance with common commercial dynamite practice. Such formulas typically consist of a liquid sensitizer, in this case mixture of trimethylolethane trinitrate and diethylene glycol dinitrate, which may be absorbed on solid ingredients such as kieselguhr, diatomaceous earth, charcoal, siliceous earth and fuller's earth or alternatively there may be added inorganic oxidizers and carbonaceous fuel.

In formulating explosive compositions, the trimethylolethane trinitrate and diethylene glycol dinitrate sensitizers are preferably used with an inorganic oxidizer salt, to compensate for the oxygen deficiency of the mixtures. Preferably, the oxidizer employed is an inorganic nitrate. Stabilizers or antacids may also be included in the compositions.

In gun propellants the products of the process of this invention may be used as energetic plasticizers to confer the same waterproofness and non-hygroscopic properties as does glycerol trinitrate and have the added advantages lower freezing point and lower flame temperatures. In addition the products do not produce the same toxic reactions in those handling the propellants as glycerol trinitrate.

Such gun propellant formulations would typically consist of the energetic plasticizer. In this case the co-nitrated trimethylolethane and diethylene glycol mixture, nitrocellulose, a stabilizer, and if desired, an inert plasticizer, solid or liquid energetic ingredients, anti-bore erosion additives, anti-fouling additives and flash suppressants. Such formulations may be extruded or cast depending on the propellant consistency and required ballistic properties.

The process of this invention will be further illustrated in the following examples.

EXAMPLE 1

Into a 15 gallon reactor fitted with cooling coils for temperature control and a stirrer for agitation are placed 130 pounds of nitric acid and sulfuric acid having the following analysis:

48.1% by weight Sulfuric acid
54.9% by weight Nitric acid
−3.0% by weight Water

To this mixture is added, slowly a solution of 14.1 pounds of trimethylolethane 16.3 pounds of diethylene glycol and 5.4 pounds of water. During the addition and reaction, the temperature is maintained at 15° C. There is an excess of 71.6% by weight of nitric acid over that stoichiometrically required for the co-nitration. The total reaction time is 60 minutes. At the end of the 60 minutes, agitation is halted, cooling stopped and the spent acid and co-nitrated esters allowed to separate under the influence of gravity for 30 minutes. The spent acid layer is removed and placed in storage where it exhibits no decomposition when stored for over 24 hours at 110° F. The co-nitrated esters are washed with 48.4 pounds of water at 40° C. for 15 minutes and allowed to separate. They are then washed with 50 pounds of 2% soda ash solution at 25° C. for 15 minutes and again allowed to separate. The resulting co-nitrated product weighs 53 pounds and has a composition of about 50% by weight of trimethylolethane trinitrate and about 50% by weight of diethylene glycol dinitrate.

When the same reaction is repeated using an excess of only 35% by weight of nitric acid over that stoichiometrically required for co-nitration the spent acid decomposed spontaneously in about 14.5 hours after the reaction @ 100° F.

EXAMPLE 2

Into a 1 liter, jacketed reactor fitted with a stirrer for agitation and a thermocouple for temperature measurement is placed 1000 grams of nitric and sulfuric acid having the following analysis:

48.65% by weight Sulfuric Acid
54.13% by weight Nitric Acid
−2.78% by weight Water To this mixture is added, slowly, a solution of 154 grams of trimethylolethane, 76 grams of diethylene glycol and 41 grams of water. During the addition and reaction, the temperature is maintained at 0°–7° C. There is an excess of 62.8% by weight of nitric acid over that stoichiometrically required for the co-nitration. The total reaction time is 83 minutes. At the end of 83 minutes, agitation is halted, cooling stopped and the reactor contents allowed to separate under the influence of gravity for 15 minutes. The spent acid layer is removed and placed in storage where it exhibits no decomposition after more than 24 hours at 110° F. The co-nitrated esters are washed with fresh water and 2% soda ash in the manner normal for explosive oils. The resulting co-nitrated product weighed 439 grams and is composed of about 70% by weight trimethylolethane trinitrate and 30% by weight diethylene glycol dinitrate.

I claim:

1. In a process of co-nitrating a mixture of trimethylolethane and diethylene glycol with a mixture of sulfuric and nitric acids, the improvement of using an excess of between about 65 to about 100% by weight of nitric acid above the stoichiometric requirement for the co-nitration.

2. The process of claim 1 wherein the ratio of trimethylolethane to diethylene glycol is from about 40 to 60% by weight to about 70 to 30% by weight.

3. The process of claim 1 wherein a storage stable spent acid is removed following the co-nitration.

* * * * *